United States Patent [19]
Harandi et al.

[11] Patent Number: 5,348,707
[45] Date of Patent: Sep. 20, 1994

[54] APPARATUS FOR ETHER PRODUCTION

[75] Inventors: Mohsen N. Harandi, Lawrenceville; Hartley Owen, Belle Mead, both of N.J.

[73] Assignee: Mobil Oil Corporation, Fairfax, Va.

[21] Appl. No.: 644,141

[22] Filed: Jan. 22, 1991

Related U.S. Application Data

[63] Continuation-in-part of Ser. No. 495,667, Mar. 19, 1990, Pat. No. 5,015,782.

[51] Int. Cl.$^5$ .............................................. B01J 8/04
[52] U.S. Cl. ...................................... 422/129; 44/449; 422/142; 422/144; 422/190; 422/211
[58] Field of Search ............... 422/142, 144, 139, 190, 422/211, 129; 568/697, 453; 44/449

[56] References Cited

U.S. PATENT DOCUMENTS 4,957,709  9/1990  Harandi ................................ 422/187
5,013,329  5/1991  Bell et al. ............................ 568/697

Primary Examiner—Timothy M. McMahon
Attorney, Agent, or Firm—Alexander J. McKillop; Malcolm D. Keen; Jessica M. Sinnott

[57] ABSTRACT

A multistage catalytic reactor system for preparing ethers such as methyl t-butyl (MTBE) and t-amyl methyl ether (TAME) from iso-olefin and methanol, comprising a first reactor for contacting the iso-olefin and alcohol with a solid regenerable catalyst, such as medium-pore zeolite conversion catalyst for partial conversion of the iso-olefin and methanol to an unsymmetrical ether, operatively connected for feeding effluent from the first reactor to a second etherification reaction zone containing sensitive catalyst, such as macroreticular polystyrenesulfonic acid resin. In a preferred embodiment, the second reaction zone comprises an inlet means for receiving withdrawn intermediate product, a catalytic distillation column containing solid acid resin etherification catalyst in a plurality of fixed bed catalysis-distillation zones, and outlet means for withdrawing a final etherification product.

10 Claims, 1 Drawing Sheet

APPARATUS FOR ETHER PRODUCTION

REFERENCE TO COPENDING APPLICATION

This application is a continuation-in-part of U.S. patent application Ser. No. 07/495,667, filed Mar. 19, 1990, U.S. Pat. No. 5,015,782.

FIELD OF THE INVENTION

The present invention relates to multi-stage catalytic reactor apparatus. More particularly it relates to a reactor system for protection of sensitive catalyst used in preparing ethers, such as methyl t-butyl ether (MTBE) and t-amyl methyl ether (TAME) production with polystyrenesulfonic acid resin.

BACKGROUND OF THE INVENTION

Catalytic reactors employing sensitive catalyst materials are found in various processes. Regeneration of industrial catalysts often require severe operating conditions, especially where the catalyst is employed in conversion of organic feedstocks and process coke or the like is removed by high temperature treatment and/or oxidative regeneration. Recent efforts have been made in the field of gasoline blending to increase gasoline octane performance without the addition of deleterious components such as tetraethyl lead and benzene. It has been found that lower molecular weight unsymmetrical ethers such as MTBE and TAME can be added to $C_5$–$C_{10}$ hydrocarbon-containing gasoline products in order to increase octane number. The research octane number (RON) of MTBE has been listed at 115 (Lander, E. P. et al, "National Petroleum Refiners Association Annual Meeting", San Francisco, Calif., Mar. 20–24, 1983). The blending octane number of MTBE has been calculated over various concentrations and some of the readings are: RON, 115–135; MON (motor octane number), 98–110; and (RON & MON)/2, 106–122.5 (Pecci, G. et al, *Hydrocarbon Processing*, 1977, 56, 98). Blending octane number rises when MTBE concentration is decreased and saturates concentration of the base fuel is increased.

Conventional etherification processing uses as catalyst a macroreticular cation exchange resin in the hydrogen form. An example of such a catalyst is "Amberlyst 15". A resin catalyst gives a high conversion rate but is unstable at elevated temperatures (above about 90° C.). When overheated, the resin catalyst releases sulfonic and sulfuric acids. In addition leaching of acid substances from the resin catalyst even at normal operating temperatures causes a reverse reaction—decomposition of ether products to starting materials—to occur upon distillation of ether product. Overall yield is thereby significantly decreased (see U.S. Pat. No. 4,182,913 to Takesono et al).

Etherification reactions conducted over a resin catalyst such as "Amberlyst 15" are usually conducted in the liquid phase below a temperature of about 90° C. and at a pressure of about 200 psig. Equilibrium is more favorable at lower temperatures but the reaction rate decreases significantly. Also excess methanol appears to be required to achieve acceptable selectivity over "Amberlyst 15" (see Chu et al, *Industrial Engineering and Chemical Research*, Vol. 26, No. 2, 1987, 365–369).

Some recent efforts in the field of etherification reactions have focused on the use of acid medium-pore zeolite catalyst for highly selective conversion of iso-olefin and alcohol starting materials. Examples of such zeolite catalysts are ZSM-4, ZSM-5. ZSM-11, ZSM-12, ZSM-23, ZSM-35, ZSM-50 and zeolite Beta. Due to lower acidity as compared to resin catalysts, the zeolites need to be employed at higher reaction temperature to achieve the desired conversion rates. These solid acid catalyst particles are much more thermally stable than resin catalyst, are less sensitive to methanol-to-isobutene ratio, give no acid effluent, and are easily and quickly regenerated (see Chu et al, "Preparation of Methyl tert-Butyl Ether (MTBE) over Zeolite Catalysts", *Industrial Engineering and Chemical Research*, op cit.).

Certain processes, such as MTBE production, can employ catalyst packed in a distillation column to achieve reaction and distillation concurrently in the same unit operation. This technique is disclosed in U.S. Pat. Nos. 4,215,011 and 4,232,177 (Smith) and 4,935,577 (Huss et al). In such configurations, in situ regeneration or reactivation of catalyst may not be feasible.

It is an object of the present invention to provide apparatus for continuous operation in preparation of t-alkyl ethers from an alcohol and an iso-olefin with a conventional acid resin catalyst whereby the resin catalyst is protected from impurities such as nitrogen compounds, metals, and coke. It is a further object to provide a multistage catalytic reactor system employing regenerable catalyst in a primary reaction zone and having non-regnerated catalyst in a secondary reaction zone.

SUMMARY OF THE INVENTION

A multistage catalytic reactor system is provided for continuous chemical reaction comprising: first stage reactor means for contacting a feedstock under partial reaction conditions in a first reaction zone containing regenerable solid catalyst to convert a portion of the feedstock to product; means for recovering a reactant effluent from the first stage containing product, unreacted feedstock; secondary stage reactor means for converting at least a portion of first stage effluent in a second stage, such as a catalytic distillation column containing non-regenerated solid catalyst in a plurality of fixed bed catalysis-distillation zones, to complete substantially full reaction of feedstock; means for recovering product as a bottom liquid stream from the catalytic distillation column; and means for regenerating the first stage catalyst to restore catalytic activity for continuing production with regenerated catalyst.

DRAWING

The single FIGURE is a schematic diagram of a preferred embodiment of the present reactor system, showing major operating units and flow of reactants and chemical products.

DETAILED DESCRIPTION OF THE INVENTION

Figure 1:
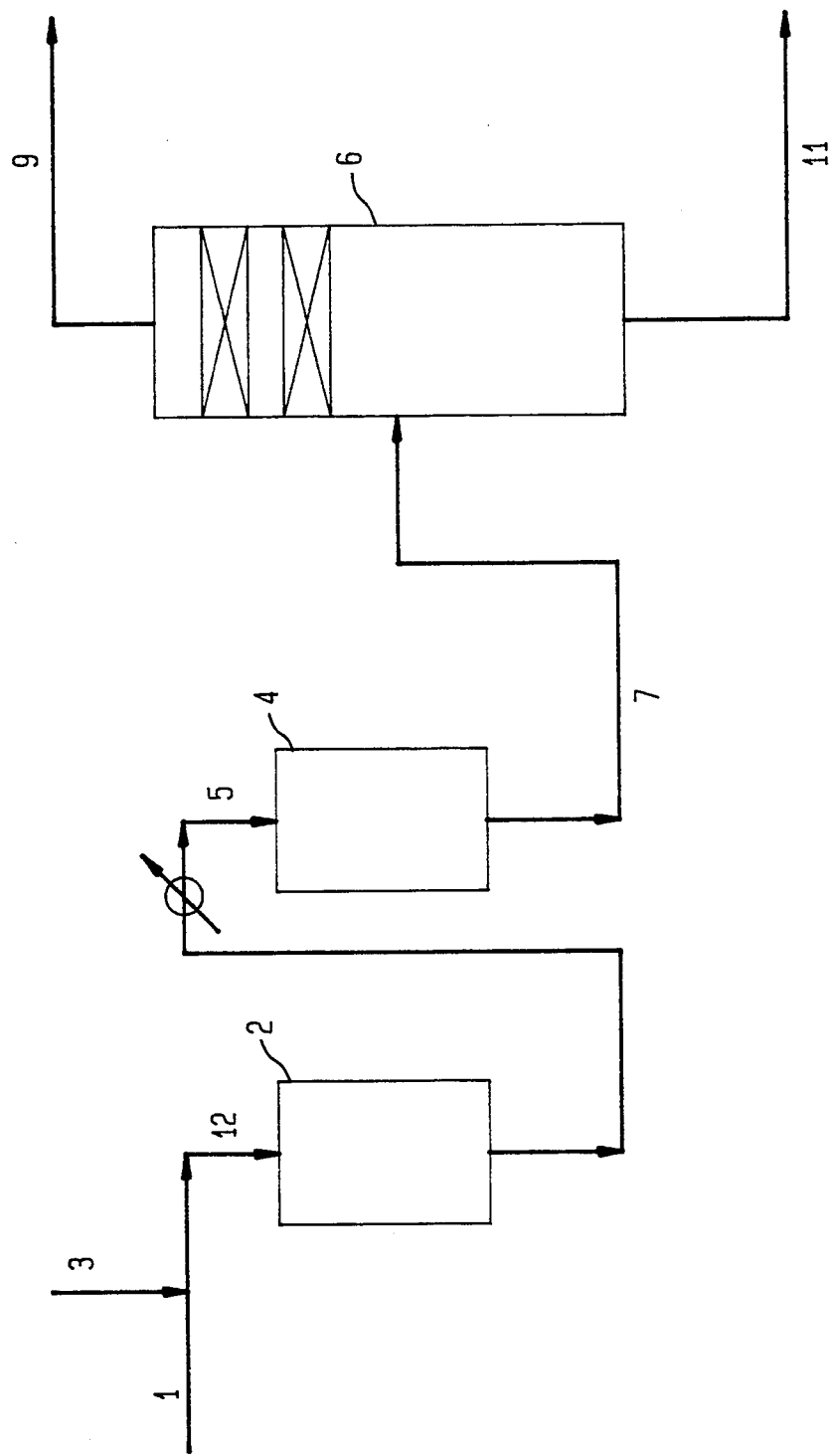

In a preferred embodiment, the present inventive system relates to the preparation of MTBE wherein selectivity and yield are increased and destruction of resin catalyst is greatly decreased. Two reaction zones are maintained in series arrangement. A first reaction zone contains solid crystalline acid medium-pore metallosilicate catalyst particles. A second reaction zone contains acid resin catalyst. Mixed feedstock containing methanol and isobutene-containing $C_4$ hydrocarbons is contacted with solid catalyst particles in the first reaction zone under etherification conditions to obtain an intermediate product comprising MTBE and unreacted feedstock. The intermediate product is then withdrawn from the first reaction zone and added to the second zone for contact with acid resin catalyst under etherification conditions. A product containing a major amount of MTBE is then withdrawn from the second reaction zone. The product is fractionated to obtain a purified MTBE which is recovered.

In this description, metric units and parts by weight are employed unless otherwise stated.

A preferred reactor system comprises means for removing the first reaction zone from on-line contact with the feedstock, regenerating the solid catalyst particles in the first reaction zone, and resuming addition of feedstock to the first reaction zone. This may be achieved with a conventional swing reactor system (see Owen et al, U.S. Pat. No. 4,456,779, incorporated by reference). The preferred solid acid catalyst particles are aluminosilicate zeolites selected from ZSM-5, ZSM-11, ZSM-50 and zeolite Beta. Since the mixed olefinic feedstock contains many impurities, even after treatment in a "Merox" unit and a water wash, the solid acid zeolite catalyst becomes highly contaminated after a period of on-line contact with feedstock. Some of the impurities which are absorbed on the zeolite particles are: nitrogen compounds; metals such as Al, Fe, Na and Mg; and oligomers of olefins and diolefins, such as isoprene and cyclopentadiene. Diolefinic compounds and other related hydrocarbons are deposited as coke on the surface and interstices of the zeolite and/or resin catalytic particles. It is therefore an objective of the present process to remove feedstock impurities in the first reaction zone concurrently with the preparation of ethers.

The first reaction zone preferably comprises a plurality of catalytic fixed bed reactors operatively connected for swing from production mode to regeneration mode in alternating sequence. A continuous operation is thus maintained when a fixed bed must be removed from service for catalyst to be regenerated. In one embodiment of the process, the first reaction zone comprises at least three catalytic fixed bed reactors whereby two reactors remain operative at all times. Thus iso-olefin-containing feedstock and alcohol contact acid medium-pore zeolite catalyst in a sequential fashion in the first reaction zone.

In an alternative embodiment, the first reaction zone contains reactors other than fixed bed, such as moving bed, slurry, fluidized bed, or ebullated bed. A suitable vapor phase zeolite catalyst reactor is disclosed by Owen et al in U.S. Pat. No. 4,831,203, incorporated by reference. It is within the scope of the present process and apparatus to adjust the number and types of reactors which contain acid zeolite catalyst in order to optimize both product yield and overall energy consumption as would be practiced by one skilled in the art.

Catalyst regeneration can be achieved by contacting contaminated zeolite catalyst particles with oxygen or oxygen-containing gas in a regeneration zone under conditions of temperature and pressure sufficient to remove at least a major amount of impurities from the catalyst particles. Typical oxidative regeneration conditions are 700°–950° F. and 0–200 psig. In an alternative embodiment zeolite catalyst particles can be regenerated by stripping with a hot stream of hydrogen gas at a temperature of about 700° F. to 1000° F. Hydrogen stripping avoids the problem of inactivating the catalyst by "steaming" which can occur under oxidative regeneration conditions due to water formation.

Since zeolite catalyst particles are readily regenerated, the mixed olefinic feedstock can contain a significant amount of impurities. If desired, the step of washing the feedstream with water can be eliminated. Isobutene-containing feedstreams of low quality can be employed in resin-catalyzed etherification reactions if said feedstreams are first contacted with zeolite catalytic particles such as ZSM-5 under conditions of the present process.

The second reaction zone contains an acid resin catalyst which is preferably a macroreticular polystyrene sulfonic acid resin catalyst. In a preferred embodiment the second reaction zone contains a catalytic distillation column containing polystyrenesulfonic acid resin catalyst in a plurality of fixed bed catalysis-distillation units located in the upper half of the distillation column. The reaction section column is preferably operated at a temperature about 10° to 30° C. lower than the temperature of the first reaction zone.

In an alternate embodiment, the second reaction zone is not a catalytic distillation column, but rather a single reactor or plurality of reactors. Reactor configuration can take many forms, for example, fixed bed, stirred slurry (see U.S. Pat. No. 3,940,450 to Lee, incorporated herein by reference), swing or ebullated bed. It is within the scope of the present process to employ for the second reaction zone any reactor configuration for sequencing acceptable to the skilled engineer. The present invention contemplates that an acid resin catalyst be employed following a regenerable etherification catalyst, preferrably in the second reaction zone. In a preferred embodiment, the resin catalyst is "Amberlyst 15".

The present process is an improvement in the conventional process for producing an ether by reacting an olefinic feedstock with an alcohol. The conventional reaction is conducted in the presence of a solid etherification catalyst of the sulfonic resin type in acid form and the olefinic feedstock contains impurities which substantially reduce the activity of the resin catalyst.

The improvement of the present process comprises adding a preliminary step of contacting the olefin and alcohol reactants in the liquid phase with oxidatively regenerable solid acid catalyst particles in a preliminary reaction zone under partial etherification conditions to produce an intermediate stream comprising tert-alkyl ether and unreacted olefin and alcohol, said intermediate stream being substantially free from impurities which reduce catalyst activity. In a preferred embodiment the olefinic feedstock comprises isobutene in an amount of at least about 10 wt. %. Preferably the acid catalyst is aluminosilicate having the structure of ZSM-5 or zeolite Beta and is contained in a swing reactor or slurry type reactor for ease of removal from contact with reactants. Once removed from on-line activity, the acid catalyst is easily regenerated at elevated temperature.

Although the preferred alcohol is methanol, suitable substitutes include ethanol or isopropanol (isopropyl alcohol). Of course, use of these substitutes will yield different ether products. It is within the scope of the present process to employ a mixture of lower molecular weight alcohols. Although isobutene is the preferred hydrocarbon feed, other iso-olefin such as 3-methyl-2-butene can be etherified in the present process.

An apparatus for catalytically preparing ethers from olefins and alcohols is presently disclosed. The apparatus comprises a first reaction zone comprising an inlet means for receiving a mixed feedstock comprising olefins and alcohols, a reactor system containing solid acid medium-pore zeolite catalyst particles, and an outlet means for withdrawing intermediate product comprising ethers and unreacted feedstock. Said apparatus further comprises a secondary reaction zone comprising an inlet means for receiving withdrawn intermediate product, a catalytic distillation column containing solid acid resin etherification catalyst in a plurality of fixed bed catalysis distillation zones, and an outlet means for withdrawing a final etherification product. Also included in the apparatus is a means for transferring intermediate product from the first reaction zone to the second reaction zone.

Referring to the FIGURE, a pre-washed $C_4$ hydrocarbon feedstock which can contain impurities is combined as by line 1 with a lower molecular weight alcohol feed which passes through line 3. The combined stream enters reaction zone 2 as by line 12. A regenerable solid metal oxide acid catalyst such as ZSM-5 is contained in reaction zone 2. The mixed alcoholic $C_4$ hydrocarbon feedstream contacts the solid catalyst within the reaction zone 2 at predetermined reaction zone conditions of temperature and pressure to convert at least a portion of the feedstream to MTBE. Impurities present within the feedstock are effectively removed from the partially converted feedstream by the solid acid catalyst.

A first intermediate stream containing MTBE and unreacted $C_4$ hydrocarbons and alcohol is cooled before entering reaction zone 4 as by line 5. Reaction zone 4 contains a solid regenerable metal oxide acid catalyst such as ZSM-5. The first intermediate stream contacts solid catalyst under etherification conditions to obtain MTBE. Any impurities contained in the first intermediate stream are adsorbed by the solid catalyst.

Regeneration of the solid acid catalyst in both reaction zones 2 and 4 is accomplished by procedures well-known in the art. A series of swing reactors can be employed, whereby a reactor containing contaminated de-activated catalyst can be easily removed from the process and replaced immediately with a reactor containing active catalyst. Reaction zones 2 and 4 can be serially arranged catalytic fixed bed reactors or combined into a single moving bed, slurry, or ebullated bed reaction zone. The catalytic material, preferably ZSM-5, can be regenerated by contact with oxygen or an oxygen-containing gas at elevated temperatures.

A second intermediate stream containing MTBE and unreacted $C_4$ hydrocarbons and alcohol is withdrawn from reaction zone 4 and enters catalytic distillation column 6 as by line 7. In a preferred embodiment, the temperature of second intermediate stream is reduced prior to entering the distillation column. In distillation column 6 a substantial portion of unreacted $C_4$ hydrocarbons and alcohols are converted to MTBE over a polystyrenesulfonic acid resin catalyst such as "Amberlyst 15". Etherification over resin catalyst is carried out preferably at a temperature of about 37° to 75° C. and a pressure of about 10 to 350 psig. In a preferred embodiment acid resin catalyst is placed in the rectifying section of a debutanizer column used for stabilizing the ethers. A product stream comprising MTBE can be withdrawn from distillation column 6 by line 11. Unreacted light gases are removed as by line 9.

To illustrate the common problem of catalyst poisoning when a polysulfonic acid resin catalyst is employed in the etherification process, MTBE resin catalyst unit is operated in a continuous fashion for a period of six months. Isobutene containing hydrocarbon feed is purified in a "Merox" unit and water-washed prior to entering the MTBE reactor. Conversion decreases from 93% to 52% during the six month period. Analysis identifies the contaminants on the resin catalyst. The major contaminants are nitrogen compounds, which are responsible for about 60% of the catalyst deactivation. The concentration of nitrogen on the deactivated resin catalyst is about $25 \times 10^3$ ppm. Metals such as Al, Fe, Na and Mg account for about 10% of the deactivation. The source of such metals is mainly from the water wash tower. The concentration of the metals on the deactivated catalyst is about $15 \times 10^2$ ppm. The third type of contaminant is coke. Coke is formed on the resin catalyst due to the presence of such compounds as cyclopentadiene and isoprene in the hydrocarbon feedstock. Continuous monitoring of the feedstock is necessary to control particularly the diolefinic $C_5$ hydrocarbon content. One of the advantages of the present process is that coke formation occurs primarily on the zeolite catalyst. Oxidative regeneration or hydrogen stripping of zeolite catalyst can then effectively remove the coke and nonmetallic contaminants from the etherification catalyst.

It is also observed that acetone and nitrile compounds were major contaminants in the hydrocarbon feedstocks which have been water washed. For example, a feed sample may contain 190 ppm acetone, 3 ppm acetonitrile and 16 ppm propionitrile. An advantage of the present process is that the hydrocarbon feedstock does not have to be water washed.

While the invention has been described by specific examples and embodiments, there is no intent to limit the inventive concept except as set forth in the following claims.

We claim:

1. An apparatus for catalytically preparing ethers from olefins and alcohols comprising:
   a first reaction zone comprising an inlet means for receiving a mixed feedstock comprising olefins and alcohols, a reactor system containing solid acid medium-pore zeolite catalyst particles, the reactor system comprising a plurality of fixed bed catalyst zones operatively connected for swing from production mode to regeneration mode in alternating sequence, and an outlet means for withdrawing intermediate product comprising ethers and unreacted feedstock;
   a second reaction zone comprising an inlet means for receiving withdrawn intermediate product, a catalytic distillation column containing solid acid resin etherification catalyst in a plurality of fixed bed catalysis-distillation zones, and outlet means for withdrawing a final etherification product; and
   means for transferring intermediate product from the first reaction zone to the second reaction zone.

2. A multistage reactor system for etherifying a mixed $C_4^+$ olefinic hydrocarbon feedstock containing isoalkene, comprising:
   first stage reactor means for contacting the olefinic feedstock and aliphatic alcohol under partial etherification conditions in a first reaction zone containing regenerable inorganic metal oxide acid solid catalyst to convert a major amount of the isoalkene to $C_5^+$ tertiary-alkyl ether, the first stage reactor means comprises a plurality of fixed bed catalyst zones operatively connected for swing from product mode to regeneration mode in alternating sequence;

means for recovering a reactant effluent from the first stage containing ether product, unreacted alcohol and unreacted olefin including isoalkene;

secondary stage reactor means for first stage effluent in a second stage catalytic distillation column containing solid acid resin etherification catalyst in a plurality of fixed bed catalysis-distillation zones to complete substantially full etherification of isoalkene;

means for recovering $C_5^+$ ether as a liquid from the catalytic distillation column; and means for regenerating the first stage catalyst to remove feedstock impurity and coke and to restore acid activity and continuing ether production with regenerated catalyst.

3. The system of claim 2 wherein the first stage catalyst comprises oxidatively regenerable medium pore zeolite and the secondary stage catalyst comprises polymeric sulfonic acid resin.

4. The system of claim 2 wherein the first stage reactor means comprises at least two serial reactor zones, and including means for maintaining at least one first stage reactor zone at least 5° C. higher than said secondary reactor means.

5. Continuous multistage reactor apparatus for preparing ether comprising:

at least two reaction zones in series arrangement, including a first reaction zone containing solid crystalline acid medium pore metallosilicate catalyst particles the first reaction zone comprising a plurality of catalyst zones operatively connected for swing from production mode to regeneration mode in alternating sequence and a second reaction zone containing acid resin catalyst.

means for contacting a mixed feedstock comprising alcohol and olefinic hydrocarbon with the solid metallosilicate catalyst particles in the first reaction zone under partial etherification conditions to obtain an intermediate ether stream containing unreacted feedstock;

means for withdrawing intermediate product from first reaction zone; and means for contacting intermediate product with acid resin catalyst in the second zone under substantially complete etherification conversion conditions to obtain a product ether.

6. Apparatus according to claim 5 further comprising means for withdrawing the product from the second reaction zone as a product stream comprising a major amount of ether; and fractionation means operatively connected to receive said product stream from the second reaction zone for recovering purified ether.

7. Apparatus according to claim 5 wherein the solid acid catalyst particles comprise aluminosilicate zeolite having the structure of ZSM-5, ZSM-11, ZSM-50 or zeolite Beta.

8. Apparatus according to claim 5 wherein the acid resin catalyst comprises macroreticular polystyrenesulfonic acid catalyst.

9. A multistage catalytic reactor system for continuous chemical reaction comprising:

first stage reactor means for contacting a feedstock under partial reaction conditions in a first reaction zone containing regenerable solid catalyst to convert a portion of the feedstock to product the first reaction zone comprising a plurality of fixed bed catalyst zones operatively connected for swing from production mode to regeneration mode in alternating sequence;

means for recovering a reactant effluent from the first stage containing product, unreacted feedstock;

secondary stage reactor means for converting at least a portion of first stage effluent in a second stage catalytic distillation column containing non-regenerated solid catalyst in a plurality of fixed bed catalysis-distillation zones to complete substantially full reaction of feedstock;

means for recovering product as a bottom liquid stream from the catalytic distillation column; and means for regenerating the first stage catalyst to restore catalytic activity for continuing production with regenerated catalyst.

10. The system of claim 9 wherein the first stage catalyst comprises oxidatively regenerable medium pore zeolite and the secondary stage catalyst comprises polymeric sulfonic acid resin.

* * * * *